US011391726B2

(12) United States Patent
Lake et al.

(10) Patent No.: US 11,391,726 B2
(45) Date of Patent: Jul. 19, 2022

(54) MOT CELLS AS A THERAPEUTIC SCREENING TOOL FOR REGULATORY T-CELL ACTIVITY

(71) Applicants: ARIZONA BOARD OF REGENTS ON BEHALF OF ARIZONA STATE UNIVERSITY, Scottsdale, AZ (US); MAYO FOUNDATION FOR MEDICAL EDUCATION AND RESEARCH, Rochester, MN (US)

(72) Inventors: Douglas Lake, Scottsdale, AZ (US); Thai H. Ho, Scottsdale, AZ (US); Glen J. Weiss, Phoenix, AZ (US)

(73) Assignees: ARIZONA BOARD OF REGENTS ON BEHALF OF ARIZONA STATE UNIVERSITY, Scottsdale, AZ (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 17/256,592

(22) PCT Filed: Sep. 25, 2019

(86) PCT No.: PCT/US2019/052984
§ 371 (c)(1),
(2) Date: Dec. 28, 2020

(87) PCT Pub. No.: WO2020/069000
PCT Pub. Date: Apr. 2, 2020

(65) Prior Publication Data
US 2021/0270807 A1 Sep. 2, 2021

Related U.S. Application Data

(60) Provisional application No. 62/738,043, filed on Sep. 28, 2018.

(51) Int. Cl.
G01N 33/50 (2006.01)
C12N 5/0783 (2010.01)

(52) U.S. Cl.
CPC ......... *G01N 33/505* (2013.01); *C12N 5/0637* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 8,946,186 | B2 | 2/2015 | Lake et al. |
| 9,546,370 | B2 | 1/2017 | Lake et al. |
| 10,894,034 | B2 | 1/2021 | Lake et al. |
| 2009/0186042 | A1 | 7/2009 | Johnston et al. |
| 2014/0141015 | A1 | 5/2014 | Lake et al. |
| 2021/0137883 | A1 | 5/2021 | Lake et al. |

FOREIGN PATENT DOCUMENTS

| | | |
|---|---|---|
| EP | 1930415 A1 | 9/2006 |
| WO | 2009126718 A2 | 10/2009 |
| WO | 2010071787 A1 | 6/2010 |
| WO | 2010071788 A1 | 6/2010 |
| WO | 2010077921 A1 | 7/2010 |
| WO | 2021077031 A1 | 4/2021 |

OTHER PUBLICATIONS

Pedersen et al., 2015, Immunopharm. immunotox. vol. 37: 63-71.*
ATCC product information for Mo T, CRL-8066, 2021, pp. 1-6.*
Saxon, A, et al., Immunologic Characterization of Hair Cell Leukemias in Continuous Culture, The Journal of Immunology, 1978, vol. 120, No. 3, pp. 777-782.
Hill, E., "Inhibition of activation induced CD154 on CD4+ CD25− Cells: a valid surrogate for human Treg suppressor function", Immunology and Cell Biology, 2012, vol. 90, pp. 812-821.
Asseman C, et al. An essential role for interleukin 10 in the function of regulatory T cells that inhibit intestinal inflammation. J Exp Med 1999; 190(7): 995-1004.
Ballard DW, et al. HTLV-I tax induces cellular proteins that activate the kappa B element in the IL-2 receptor alpha gene. Science 1988; 241(4873): 1652-5.
Battaglia M, et al. Rapamycin selectively expands CD4+CD25+ FoxP3+ regulatory T cells. Blood 2005; 105(12): 4743-8.
Bausch-Fluck D, et al. A mass spectrometric-derived cell surface protein atlas. PLoS One 2015; 10(3): e0121314.
Belkaid Y, et al. Natural regulatory T cells and parasites: a common quest for host homeostasis. Immunol Rev 2006; 212: 287-300.
Bluestone JA, et al. Type 1 diabetes immunotherapy using polyclonal regulatory T cells. Sci Transl Med 2015; 7 (315): 315ra189.
Campbell DJ, et al. Phenotypical and functional specialization of FOXP3+ regulatory T cells. Nat Rev Immunol 2011; 11(2): 119-30.
clincaltrials.gov. Safety and Efficacy of CLBS03 in Adolescents With Recent Onset Type 1 Diabetes (The Sanford Project T-Rex Study). 2021.
Collison LW, et al. The inhibitory cytokine IL-35 contributes to regulatory T-cell function. Nature 2007; 450(7169): 566-9.
Ezzelarab MB, et al. Adoptive Cell Therapy with Tregs to Improve Transplant Outcomes: The Promise and the Stumbling Blocks. Curr Transplant Rep 2016; 3(4): 265-274.

(Continued)

*Primary Examiner* — Amy E Juedes
(74) *Attorney, Agent, or Firm* — Quarles & Brady, LLP

(57) ABSTRACT

The present invention includes a method for screening one or more agents that modulate Regulatory T cell (Treg) activity, the method comprising the steps of: incubating a population CD4+ cells isolated from human blood peripheral mononuclear cells the CD4+ cells in contact with MoT cells in the presence of the one or more agents suspected of modulating Treg activity; detecting activation of the CD4+ cells without or with the agent; and comparing the activation of the CD4+ cells without or with the agent, wherein a change in activation following incubation with the agent relative to the activation of the PBMCs following incubation without the agent indicates that the agent is a modulator of Treg activity.

23 Claims, 8 Drawing Sheets

(56) References Cited

OTHER PUBLICATIONS

Fallarino F, et al. Modulation of tryptophan catabolism by regulatory T cells. Nat Immunol 2003; 4(12): 1206-12.
Fisher SA, et al. Increased regulatory T cell graft content is associated with improved outcome in haematopoietic stem cell transplantation: a systematic review. Br J Haematol 2017; 176(3): 448-463.
Hamano R, et al. Characterization of MT-2 cells as a human regulatory T cell-like cell line. Cell Mol Immunol 2015; 12 (6): 780-2.
Hill JA, et al. Foxp3 transcription-factor-dependent and -independent regulation of the regulatory T cell transcriptional signature. Immunity 2007; 27(5): 786-800.
International Searching Authority. International Search Report and Written Opinion for application PCT/US2019/052984. dated Nov. 4, 2019. 7 pages.
Lanteri MC, et al. Tregs control the development of symptomatic West Nile virus infection in humans and mice. J Clin Invest 2009; 119(11): 3266-77.
Nishikawa H, et al. Regulatory T cells in tumor immunity. Int J Cancer 2010; 127(4): 759-67.
Plitas G, et al. Phase I/II study of mogamulizumab, an anti-CCR4 antibody targeting regulatory T cells in advanced cancer patients. J Clin Oncology 2016; 34: 15—Supplemental.
Roychoudhuri R, et al. The interplay of effector and regulatory T cells in cancer. Curr Opin Immunol 2015; 33: 101-11.
Sauer S, et al. T cell receptor signaling controls Foxp3 expression via PI3K, Akt, and mTOR. Proc Natl Acad Sci U S A 2008; 105(22): 7797-802.
Schneider U, et al. Characterization of EBV-genome negative "null" and "T" cell lines derived from children with acute lymphoblastic leukemia and leukemic transformed non-Hodgkin lymphoma. Int J Cancer 1977; 19(5): 621-6.
Shevach EM. From vanilla to 28 flavors: multiple varieties of T regulatory cells. Immunity 2006; 25(2): 195-201.
Strainic MG, et al. Absence of signaling into CD4(+) cells via C3aR and C5aR enables autoinductive TGF-beta1 signaling and induction of Foxp3(+) regulatory T cells. Nat Immunol 2013; 14(2): 162-71.
Suri-Payer E, et al. CD4+CD25+ T cells inhibit both the induction and effector function of autoreactive T cells and represent a unique lineage of immunoregulatory cells. J Immunol 1998; 160(3): 1212-18.
Tarasevich A, et al. Monoclonal antibody profiling of cell surface proteins associated with the viral biofilms on HTLV-1 transformed cells. Acta Virol 2015; 59(3): 247-56.
Wang W, et al. PD1 blockade reverses the suppression of melanoma antigen-specific CTL by CD4+ CD25(Hi) regulatory T cells. Int Immunol 2009; 21(9): 1065-77.
Wing K, et al. CTLA-4 control over Foxp3+ regulatory T cell function. Science 2008; 322(5899): 271-5.
Zeng H, et al. Type 1 regulatory T cells: a new mechanism of peripheral immune tolerance. Cell Mol Immunol 2015; 12(5): 566-71.

\* cited by examiner

JURKAT MoT
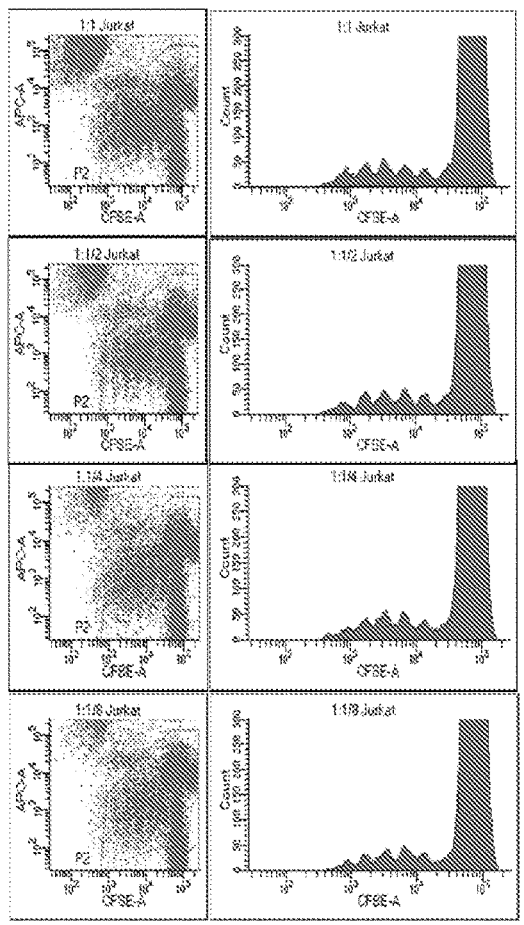
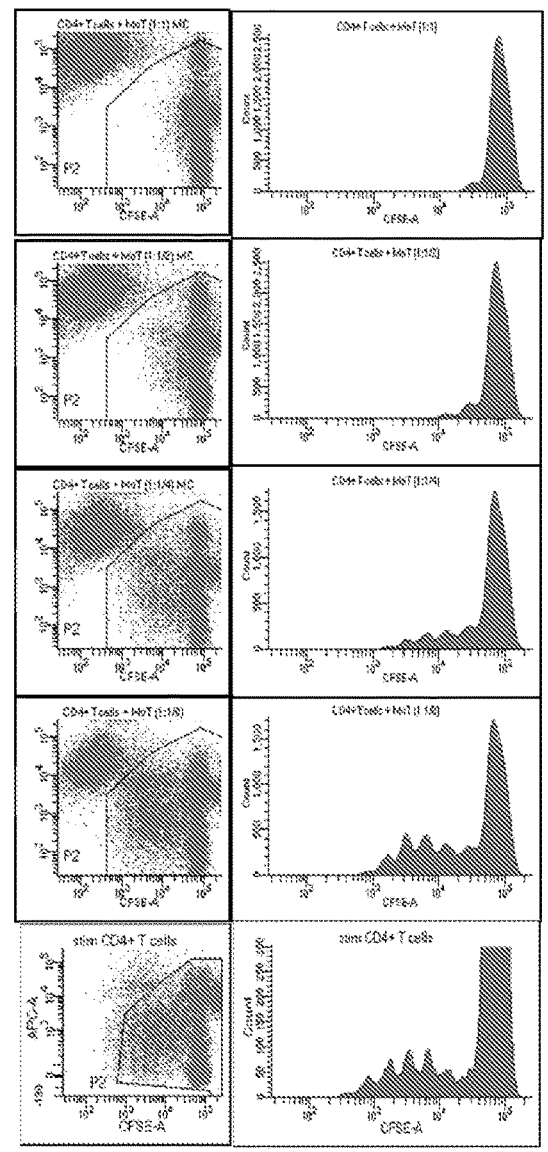
1:1
1:1/2
1:1/4
1:1/8
Stimulated CD4+ T cells-control (no co-culture)
FIG. 2

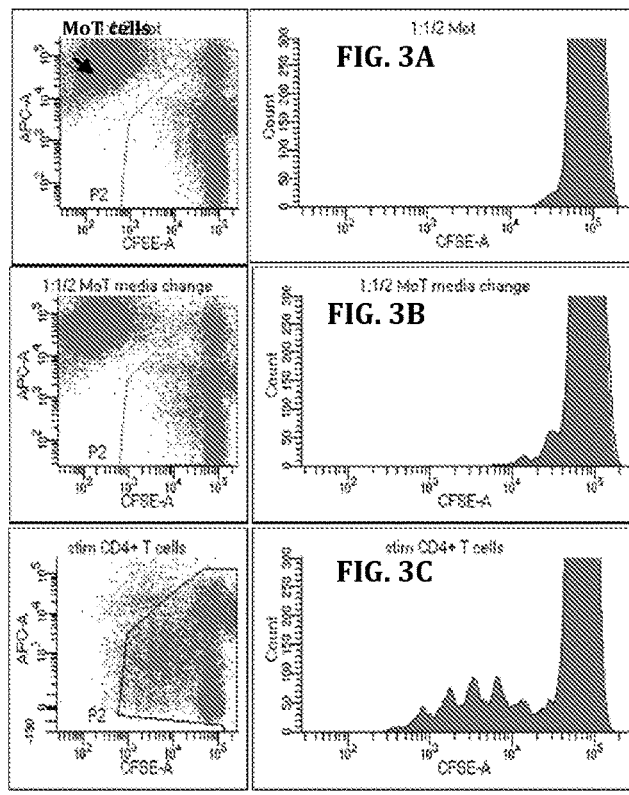
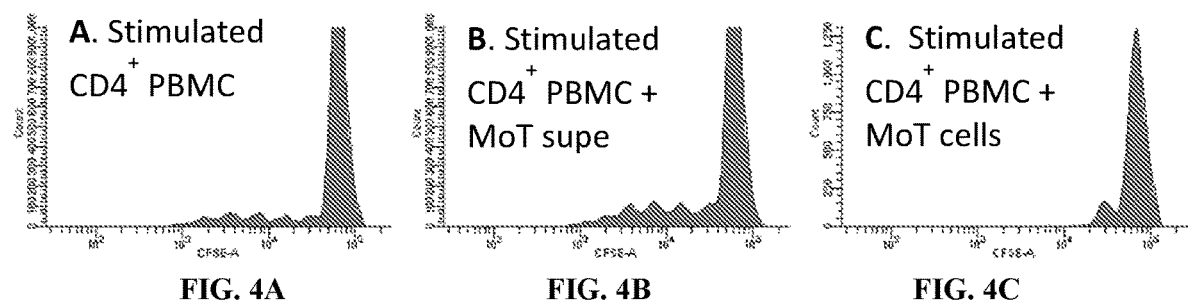
FIG. 4A     FIG. 4B     FIG. 4C

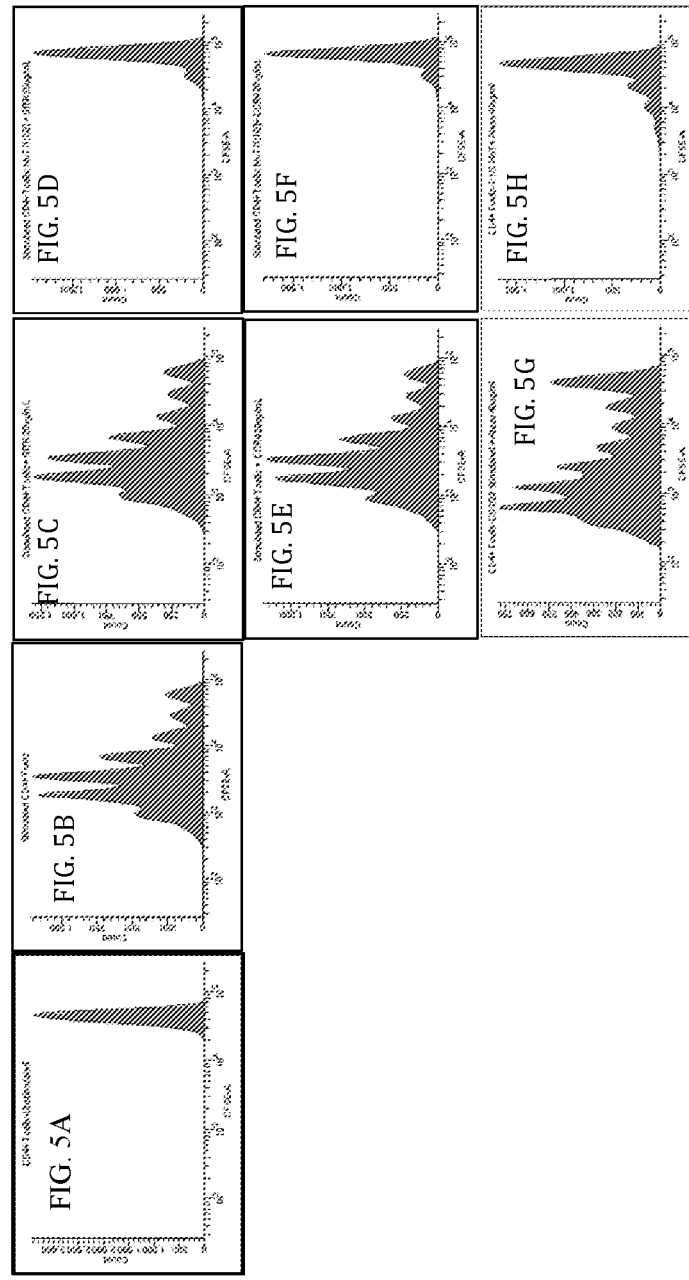

MOT CELLS AS A THERAPEUTIC SCREENING TOOL FOR REGULATORY T-CELL ACTIVITY

CROSS-REFERENCE TO RELATED APPLICATIONS

This application is a national stage filing under 35 U.S.C. § 371 of International Application No. PCT/US2019/052984, filed Sep. 25, 2019, which is a PCT patent application of and claims priority to U.S. Provisional Patent Application Ser. No. 62/738,043 filed on 28 Sep. 2018, each of which are hereby incorporated by reference in their entirety.

STATEMENT OF FEDERALLY FUNDED RESEARCH

This invention was made with government support under R01_CA224917 awarded by the National Institutes of Health. The government has certain rights in the invention.

TECHNICAL FIELD OF THE INVENTION

The present invention relates in general to the field of the screening of drugs for regulating T cell activity, and more particularly; to MoT cells as a therapeutic screening tool for Regulatory T cell (Treg) activity.

BACKGROUND OF THE INVENTION

Without limiting the scope of the invention, its background is described in connection with regulatory T cells.

Regulatory T cells (Tregs) play a crucial role in tolerance to self-antigens during T cell development in the thymus (natural/thymic Treg), after infection in the periphery (induced/peripheral Treg)[1,2] and during inflammatory processes, and cancer[3,4]. Tregs were first described as CD4+, CD25+ cells that inhibited effector function of autoreactive T cells[5]. Since then thousands of papers have been published on various activities and populations of Tregs from suppression of allergy to fetal protection to oral tolerance to protection of commensal bacteria. However, many questions remain to be answered about various subpopulations of Tregs and their function in vivo.

Characterization of thymic and peripheral Tregs is problematic due to mixed subpopulations of Tregs upon isolation from human peripheral blood and their differences in specificity and cytokine/chemokine secretion[6,7]. Tregs secrete immunosuppressive cytokines such as IL-10[8], TGF-$\beta$[3], IL-35[9] and can be found in peripheral blood as well as multiple tissues[10]. Tregs can be expanded in vitro using IL-2, TGF-$\beta$ and/or inhibition of PI3K and mTOR with single antigens from human peripheral blood, but mixed populations result[11-13]. Subpopulations of Tregs modulate TH1, TH2, and TH17 responses[10] using cell-to-cell contact[14], chemokines, cytokines, and metabolites[15]. Peripheral Treg populations, CD4+ Foxp3− regulatory T cells expressing cytokines IL-10, TGF-$\beta$, IFN-$\gamma$, IL-5, and IL-2$^{lo}$ appear to modulate peripheral immune tolerance[16]. Like other immune cell populations, Treg populations are highly heterogeneous.

Therapies that boost Treg function could inhibit pathologic immune cell function in autoimmune disease[17], decrease graft rejection in solid organ transplants[18], and decrease graft-vs-host disease in allogeneic bone marrow transplants[19]. Suppression of Tregs may also increase the anti-tumor response with immune checkpoint therapies and has been shown to increase the anti-tumor activity of CD8+ CTL[20]. However, no Food and Drug Administration (FDA) approved therapies exist that specifically either enhance or suppress Treg activity, although a phase II clinical trial is recruiting to expand Tregs to treat type 1 diabetes[21]. Treg drug development is limited in part by a requirement for large volumes of peripheral blood to isolate Tregs and their heterogeneity upon stimulation and expansion.

Thus, a need remains for a model system that permits for the identification, development, and improvement of agents that modulate Treg activity both in vitro and in vivo.

SUMMARY OF THE INVENTION

To address this clinical need, the inventors identified a human cell line, MoT (ATCC CRL-8066), with Treg-like activity. MoT cells express cell surface markers consistent with human Treg phenotypes such as: CD4, CD25, glucocorticoid induced TNF receptor (GITR), and programmed death ligand 1 (PD-L1). MoT cells weakly express FoxP3 and CCR4. Cell-cell contact is required for suppression of CD3/28-stimulated CD4+ lymphocyte proliferation by MoT; cell-free supernatant is not suppressive. To further demonstrate MoT cells as a therapeutic screening tool for Treg activity, the inventors tested the activity of anti-PD-L1, anti-GITR, and anti-CCR4, on MoT cells and did not observe restoration of peripheral blood mononuclear cell (PBMC) proliferation, perhaps suggesting an undiscovered cell surface suppressive molecule. Herein, the inventors demonstrate that MoT cells can be used as a screening tool to identify therapeutics that target or modulate Tregs.

In one embodiment, the present invention includes a method for screening one or more agents that modulate Regulatory T cell (Treg) activity, the method comprising the steps of: incubating a population CD4+ cells isolated from human blood peripheral mononuclear cells the CD4+ cells in contact with MoT cells in the presence of the one or more agents suspected of modulating Treg activity; detecting activation of the CD4+ cells without or with the agent; and comparing the activation of the CD4+ cells without or with the agent, wherein a change in activation following incubation with the agent relative to the activation of the PBMCs following incubation without the agent indicates that the agent is a modulator of Treg activity. In one aspect, the one or more agents inhibit at least one of: autoimmune disease, or graft-versus-host disease. In another aspect, the one or more agents increase an anti-tumor immune response in patients treated with, e.g., immune checkpoint inhibitor therapy. In another aspect, the MoT cell line is ATCC CRL-8066. In another aspect, the MoT cell line expresses at least one of: CD4, CD25, glucocorticoid induced TNF receptor (GITR), and programmed death ligand 1 (PD-L1), FoxP3, or CCR4. In another aspect, the activation of CD4+ cells is measured by cell proliferation. In another aspect, the activation of CD4+ cells is measured by expression of at least one of CD25, CD69, HLA-DR, CD26, or CD40L. In another aspect, the one or more agents prevent CD4+ cell apoptosis. In another aspect, the one or more agents prevent CD4+ cells from entering into Annexin V-positive and PI-negative state or early apoptosis phase. In another aspect, the one or more agents change the expression of IL17, IL17F, IL23R, RORC or IL26 is a decrease or increase in the secretion of at least one of TGFbeta, IL-1, IL-2, IL-6, or TNF following incubation with the agent, wherein the decrease indicates that the agent is an inhibitor of Treg in vitro; and the increase indicates that the agent is an activator of Treg activity in vitro. In another aspect, the one or more agents is selected from a small molecule; polypeptide; antibody; antibody fragment; azole-containing compounds; cholesterol derivative compounds; retinoid derivative compounds; shRNA/siRNA; neutralizing/blocking antibodies; tryptophan derivative compounds; Vitamin D derivatives; or molecules known to inhibit fever, inflammation, allergy, or regulatory T (Treg) cell differentiation factor. In another aspect, the method further comprises testing a combination of two or more agents to increase Treg activity, or decrease Treg activity.

In one embodiment, the present invention includes a method for screening one or more agents that modulate Regulatory T cell (Treg) activity, the method comprising the steps of: (a) providing a population CD4+ cells isolated from human blood peripheral mononuclear cells; (b) contacting the CD4+ cells with MoT cells; (c) incubating the CD4+ cells and the MoT cells in the presence of an agent suspected of modulating Treg activity; (d) detecting activation of the CD4+ cells without or with the agent; and (e) comparing the activation of the CD4+ cells without or with the agent, wherein a change in activation following incubation with the agent relative to the activation of the PBMCs following incubation without the agent indicates that the agent is a modulator of Treg activity. In one aspect, the one or more agents inhibit at least one of: autoimmune disease, or graft-versus-host disease. In another aspect, the one or more agents increase an anti-tumor immune response in patients treated with immune checkpoint therapy. In another aspect, the one or more agents are selected from an anti-PD-L1, anti-GITR, or anti-CCR4, combinations or derivatives thereof. In another aspect, the MoT cell line is ATCC CRL-8066. In another aspect, the MoT cell line expresses at least one of: CD4, CD25, glucocorticoid induced TNF receptor (GITR), and programmed death ligand 1 (PD-L1), FoxP3, or CCR4. In another aspect, the activation of CD4+ cells is measured by cell proliferation. In another aspect, the activation of CD4+ cells is measured by expression of at least one of CD25, CD69, HLA-DR, CD26, CD40L. In another aspect, the one or more agents prevent CD4+ cell apoptosis. In another aspect, the one or more agents prevent CD4+ cells from entering into Annexin V-positive and PI-negative state or early apoptosis phase. In another aspect, the one or more agents change the expression of IL17, IL17F, IL23R, RORC or IL26 is a decrease or increase in the secretion of at least one of TGFbeta, IL-1, IL-2, IL-6, or TNF following incubation with the agent, wherein the decrease indicates that the agent is an inhibitor of Treg in vitro; and the increase indicates that the agent is an activator of Treg activity in vitro. In another aspect, the one or more agents is selected from a small molecule; polypeptide; antibody; antibody fragment; azole-containing compounds; cholesterol derivative compounds; retinoid derivative compounds; shRNA/siRNA; neutralizing/blocking antibodies; tryptophan derivative compounds; Vitamin D derivatives; or molecules known to inhibit of fever, inflammation, allergy, or regulatory T (Treg) cell differentiation factor. In another aspect, the method further comprises testing a combination of two or more agents for to increase Treg activity, or decrease Treg activity.

In yet another embodiment, the present invention includes a method of evaluating a candidate drug believed to be useful in modulating Regulatory T cell (Treg) activity, the method comprising: (a) obtaining a population of CD4+ cells isolated from human blood peripheral mononuclear cells from a set of patients; (b) contacting the population of CD4+ cells isolated from human blood peripheral mononuclear cells with MoT cells from a first subset of the patients, and a placebo to the population of CD4+ cells isolated from human blood peripheral mononuclear cells with MoT cells from a second subset of the patients; (c) repeating step (b) after the administration of the candidate drug or the placebo; and (d) determining if the candidate agent activates the CD4+ cells with the agent when compared to the placebo, wherein a change in activation following incubation with the agent relative to the activation of the PBMCs exposed to the placebo indicates that the agent is a modulator of Treg activity.

BRIEF DESCRIPTION OF THE DRAWINGS

For a more complete understanding of the features and advantages of the present invention, reference is now made to the detailed description of the invention along with the accompanying figures and in which:

FIG. 2 are histograms that show five (5) day CFSE cell proliferation assays demonstrate that Jurkat cells (left column) have no suppressive anti-proliferative activity compared to MoT cells which have "cell dose-dependent" suppressive activity. Both Jurkat and MoT cells were two-fold diluted from a 1:1 ratio keeping the same number of stimulated PBMC, followed by incubation for 4 days at 37° C. in 5% $CO_2$. This stimulation induces cell division such that with every cell division, half the cell-associated CFSE dye is divided between the parent and daughter cells such that dividing cells shift left in the flow cytometry histogram. Each peak to the left of the farthest rightward peak represents one cell division. Representative data is shown from 4 experiments with 4 different donors.

FIGS. 3A to 3C show five (5) day CFSE daily media change. FIG. 3A shows no media change. FIG. 3B shows daily media change. FIG. 3C shows no media change and no MoT cells. These results demonstrate that the MoT cells are not depleting the media of nutrients.

FIGS. 4A to 4C show that MoT cell contact is required to functionally suppress proliferation of CD4$^+$ PBMC. In this assay, CFSE-labeled CD4$^+$ PBMC were stimulated with CD3 and CD28 antibodies for four days followed by flow cytometric analysis of proliferation (FIG. 4A). Four day spent supernatants from MoT cells were added to CD4+ PBMC that were stimulated with CD3/28 (FIG. 4B). MoT supernatant (FIG. 4B) stimulated 6 cell divisions while MoT cells (FIG. 4C) suppressed PBMC division compared to CD3/28 Stimulated controls (FIG. 4A). CFSE-labeled PBMC shift leftward in the flow cytometry diagram as they proliferate.

FIGS. 5A to 5H show the results from CFSE assay demonstrates that anti-PD-1/PD-L1 axis, GITR and CCR4 are not involved in suppression of CD4$^+$ PBMC proliferation by MoT cells. (FIG. 5A) Unstimulated PBMC. (FIG. 5B) CD3/28-stimulated CD4$^+$ PBMC cell division without MoT cells. (FIG. 5C) Anti-GITR, (FIG. 5E) Anti-CCR4 mogamulizumab, and (FIG. 5G) anti-PDL-1 (atezolizumab) co-incubated with PBMCs. (FIG. 5D) Anti-GITR, (FIG. 5F) anti-CCR4 (mogamulizumab), and (FIG. 5H) anti-PDL-1 (atezolizumab) co-incubated with PBMCs and MoT cells (1:1/2 ratio).

(FIG. 6A) Unstimulated CD4+ PBMCs; (FIG. 6B) anti-CD3/28-stimulated CD4+ PBMC without MoT cells; (FIG. 6C) CD4+ PBMC+MoT cells (ratio 1:1/2); (FIG. 6D) CD4+ PBMC+ Jurkat cells (ratio 1:1/2). Dot plots on the left side of each panel show CFSE-gated CD4+ PBMC. Middle dot plot shows Annexin V/PI staining of gated CD4+ PBMC. Right side of each panel shows histograms of CD4+ PBMC proliferation.

FIG. 8A represents cells from normal donor 82 and FIG. 8B represents PBMCs from an independent leukapheresis donor. This result suggests that the mechanism of MoT cell suppression is not mediated via IL-2R or LAG3 mechanisms. T cells stimulated with 5.0 ug/ml each of α-CD3 and CD28 antibody.

DETAILED DESCRIPTION OF THE INVENTION

Figure 1:
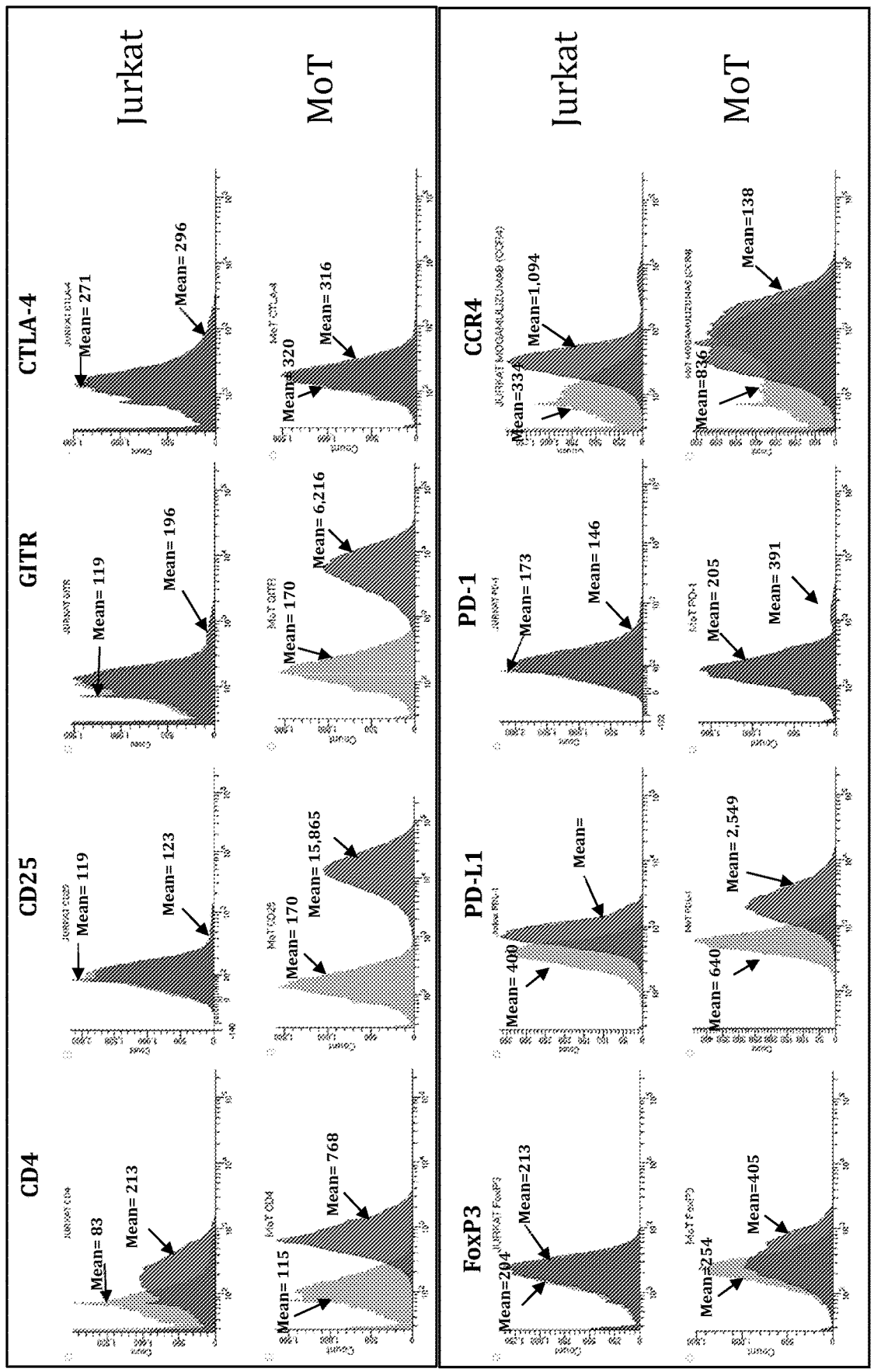
FIG. 1 includes histograms that show that MoT cells demonstrate a Treg-like phenotype. MoT cells were assessed for cell surface markers by flow cytometry: CD4, CD25, GITR, FoxP3, CTLA-4, PD-L1, and PD-1. For each histogram, mean fluorescence intensity of isotype controls is in gray on the left and specific Mab staining is shown on the right (dark purple histogram).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the terms an "agent", "active agent", "candidate compound", or "test compound" refer to, for example, proteins, peptides, peptidomimetics, antibodies, small molecules and other drugs nucleic acids (e.g., DNA and RNA), carbohydrates, lipids, azole-containing compounds, cholesterol derivative compounds, retinoid derivative compounds, short hairpin RNA (shRNA), small interfering RNA (siRNA), neutralizing and/or blocking antibodies, tryptophan derivative compounds, Vitamin D derivatives, or molecules known to inhibit fever, inflammation, or regulatory T (Treg) cell differentiation that change the activity of a target cell, e.g., a Regulatory T cell (Treg).

As used herein, the term "antibody" or "antibody molecule" refers to any immunoglobulin, including antibodies and fragments thereof, that binds to a specific antigen. The term includes polyclonal, monoclonal, chimeric, and bi-specific antibodies. An antibody or antibody molecule contemplates both an intact immunoglobulin molecule and an immunologically active portion of an immunoglobulin molecule such as those portions known in the art as Fab, Fab', F(ab')$_2$, scFv and F(v).

As used herein, the term "cell line" refers to a clone of a primary cell or cell population that is capable of stable growth in vitro for many generations. For use with the present invention, "MoT cells" refers to a human cell line MoT (ATCC CRL-8066), and mutants or derivatives of the MoT cells.

As used herein, the term "immune response" refers any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

As used herein, the terms "active agent", "candidate compound", or "test compound" identified using the method of the present invention that is a "modulator of human Treg activity". Such an agent may be identified by its ability to effect a change in Regulatory T cell (Treg) activity, such as IL17, IL17F, IL23R, RORC or IL26. As described herein, each of these cellular molecules (IL17, IL17F, IL23R, RORC or IL26) serves as a positive marker indicative of human Treg activity. Expression of IL17, IL17F, IL23R, RORC or IL26 can be induced by 10- to 100-fold in CD4+ T cells treated to promote human Treg activity relative to those treated under negative control conditions in accordance with the method of the present invention. It has been described that FOXP3 expression is correlated with human Treg activity. Accordingly, a change in the expression of at least one of these markers (positive or negative) responsive to the presence of an agent reflects a differential in human Treg activity. More particularly, a change in the expression of at least one of these markers reflects a differential in human Treg activity in a population of cells incubated in human Treg activity promoting conditions, wherein the change is dependent on incubation in the presence of a particular agent.

As used herein, the term "naive CD4+ T cells" refers to a CD4+ T cell that is functionally defined by the expression of cell surface markers of naivety that include CD3+, CD45RA+, CD8−, and HLA-DR−.

As used herein, the term "control", when used with regard to a substance, agent, or compound(s), refers to one or more molecules that is/are inert or has no activity relating to an ability to modulate a biological activity, in this case, human Treg activity and is referred to as a negative control. With respect to the present invention, such control substances are inert with respect to an ability to modulate human Treg activity in vitro. Non-limiting examples of such controls include, but are not limited to, solutions comprising physiological salt concentrations and/or buffers, or agents known to not have such any human Treg activity or an effect of human Treg activity, or in the alternative, an agent that is known to have such an effect on human Treg activity, which is a positive control.

In certain embodiment, the MoT cell line expresses at least one of: CD4, CD25, glucocorticoid induced TNF receptor (GITR), and programmed death ligand 1 (PD-L1), FoxP3, or CCR4. The activation of CD4+ cells can be measured by, e.g., expression of at least one of CD25, CD69, HLA-DR, CD26, CD40L, T cell proliferation, or preventing CD4+ cell apoptosis. The method can be used with one or more agents that change the expression of IL17, IL17F, IL23R, RORC or IL26 is a decrease or increase in the secretion of at least one of TGFbeta, IL-1, IL-2, IL-6, or TNF following incubation with the agent, wherein the decrease indicates that the agent is an inhibitor of Treg in vitro; and the increase indicates that the agent is an activator of Treg activity in vitro. In another aspect, the one or more agents is selected from a small molecule; polypeptide; antibody; antibody fragment; azole-containing compounds; cholesterol derivative compounds; retinoid derivative compounds; shRNA/siRNA; neutralizing/blocking antibodies; tryptophan derivative compounds; Vitamin D derivatives; or molecules known to inhibit of fever, inflammation, allergy, or regulatory T (Treg) cell differentiation factor.

The inventors identified a human cell line, MoT (ATCC CRL-8066), with Treg-like activity. MoT cells express cell surface markers consistent with human Treg phenotypes such as: CD4, CD25, glucocorticoid induced TNF receptor (GITR), and programmed death ligand 1 (PD-L1). MoT cells weakly express FoxP3 and CCR4. Cell-cell contact is required for suppression of CD3/28-stimulated CD4+ lymphocyte proliferation by MoT; cell-free supernatant is not suppressive. To further demonstrate MoT cells as a therapeutic screening tool for Treg activity, the inventors tested the activity of anti-PD-L1, anti-GITR, and anti-CCR4, on MoT cells and did not observe restoration of peripheral blood mononuclear cell (PBMC) proliferation, perhaps suggesting an undiscovered cell surface suppressive molecule. Herein, the inventors demonstrate that the MoT cells could be utilized as a screening tool to identify therapeutics that target or modulate Tregs.

Flow cytometry. MoT cells were maintained in IMDM (Gibco; Grand Island, N.Y.) supplemented with 10% heat-inactivated fetal bovine serum (Atlanta Biologicals; Norcross, Ga.). $5 \times 10^5$ MoT cells per 12×75 mm flow tube were washed in PBS and incubated individually with each antibody to CD4 (eBioscience clone RPA-T4), CD25 (eBioscience clone BC96), GITR (eBioscience clone eBioAITR), CTLA-4 (BD Biosciences clone BN13), PD-1 (Cell Signaling clone D3W4U), PD-L1 (Cell Signaling clone E1L3N), CCR4 (Creative Biolabs, mogamulizumab), and FoxP3 (eBioscience clone PCH101). For FoxP3 staining, cells were permeabilized with the Foxp3 Transcription Factor Buffer Staining Set (eBioscience).

Suppression assays. After IRB approval at Arizona State University (protocol #0601000548), peripheral blood was collected from healthy donors. After Ficoll-Paque Plus gradient separation of the buffy coat, CD4+ cells were purified using EasySep Human CD4+ T Cell Isolation Kit (Catalog #17952 from Stemcell Technologies). Cells were allowed to rest overnight in cIMDM at 37° C. prior to labeling with CFSE (Carboxyfluorescein succinimidyl ester, from Cayman Chemica cat #10009853) dye to track cell divisions. The following day, CD4+ T cells were counted, stained with CFSE, washed in PBS and then plated in IMDM with 10% FBS at $3 \times 10^5$ cells per well in a 48-well plate coated with OKT3 antibody at 5.0 ug/mL for 2 hours at 37° C. then washed twice in PBS before adding soluble co-stimulatory anti-CD28 (eBioscience clone CD28.6) at 5.0 ug/mL final concentration.

In some studies MoT and Jurkat cells were labeled with Cell Trace FarRed dye (Thermofisher) to gate MoT and Jurkat cells away from CD4+ PBMC in flow cytometry analysis. Two-fold serial dilutions of MoT and Jurkat cells were added to CD4+ PBMC, starting at $1.5 \times 10^5$ MoT and Jurkat cells (1:1/2 ratio CD4+ T cells:tumor cells). Final volume per well was 1 mL. Cells were incubated for 5 days. To prove that MoT cells did not consume all the nutrients, media was changed every day. On the day 5 of culture, cells were collected into individual flow tubes and washed twice in 2% FBS/PBS and placed on ice prior to analysis by flow cytometer (BD FACSCelesta).

In studies to determine if atezolizumab, mogamulizumab or anti-GITR Mabs could attenuate the suppression of MoT cells, thereby restoring CD4+ PBMC proliferation, the Mabs were pre-incubated with MoT cells for 30 minutes, then the treated MoT cells were added to CD4+ PBMCs.

MoT cells express known Treg cell surface markers. To determine if MoT cells express known Treg cell surface markers, cells were stained with antibodies specific for known Treg phenotypic cell surface markers. As shown in FIG. 1, MoT cells express cell surface CD4, CD25, GITR, and PD-L1. The inventors observed weak expression of CCR4 and the intranuclear transcription factor, FoxP3. Immunoblot confirms the weak expression of Foxp3 (Supplementary Figure at end of manuscript).

FIG. 1 includes histograms that show that MoT cells demonstrate a Treg-like phenotype. MoT cells were assessed for cell surface markers by flow cytometry: CD4, CD25, GITR, FoxP3, CTLA-4, PD-L1, and PD-1. For each histogram, mean fluorescence intensity of isotype controls is in gray on the left and specific Mab staining is shown on the right (dark purple histogram).

MoT cells suppress PBMC proliferation. A hallmark of Tregs is their ability to functionally suppress activated T cell proliferation. MoT cells were compared with another CD4+ acute T cell leukemia cell line, Jurkat[22], for the ability to suppress PBMCs proliferation. To determine if MoT cells have suppressive activity, the inventors co-cultured MoT or Jurkat cells with CD3/28-stimulated CD4+ cells purified from healthy donor PBMCs. MoT cells, but not Jurkat cells, inhibited proliferation of stimulated PBMCs in a PBMC:MoT ratio-dependent manner (FIG. 2). Serial dilutions of MoT cells attenuated the ability of MoT cells to suppress CD3/28-stimulated CD4+ PBMCs in a cell dose-dependent manner. In contrast, Jurkat cells have little to no suppressive activity even at the highest ratio of 1:1.

FIG. 2 are histograms that show five (5) day CFSE cell proliferation assays demonstrate that Jurkat cells (left column) have no suppressive anti-proliferative activity compared to MoT cells which have "cell dose-dependent" suppressive activity. Both Jurkat and MoT cells were two-fold diluted from a 1:1 ratio keeping the same number of PBMC, followed by incubation for 4 days at 37° C. in 5% $CO_2$. This stimulation induces cell division such that with every cell division, half the cell-associated CFSE dye is divided between the parent and daughter cells such that dividing cells shift left in the flow cytometry histogram. Each peak to the left of the farthest rightward peak represents one cell division. Representative data is shown from 4 different donors.

Although both MoT and Jurkat have a similar doubling time, the inventors wanted to ensure that MoT cells were not depleting the co-culture of nutrients. A study was performed in which media in the co-culture was changed daily for 5 days (FIGS. 3A to 3C). No significant difference in suppression of CD4+ PBMCs proliferation by MoT was observed between daily media change and no media change.

FIGS. 3A to 3C show five (5) day CFSE daily media change. FIG. 3A shows no media change. FIG. 3B shows daily media change. FIG. 3C shows no media change and no MoT cells.

Cell to cell contact is required for MoT Treg suppressive activity. To determine if suppressive cytokines or other soluble factors might be responsible for the inhibition of proliferation observed in the co-culture experiment in FIG. 2, the inventors harvested spent MoT supernatant and added it to $CD4^+$ PBMC. Four-day spent supernatant from MoT was directly added to activated $CD4^+$ T cells from PBMCs. When compared to CD3/28-stimulated PBMC controls, MoT supernatant stimulated 6 cell divisions while MoT cells suppressed PBMC division (FIGS. 4A to 4C). These data demonstrates cell-to-cell contact, not a soluble factor, is required for Treg suppressive activity since MoT supernatants do not inhibit proliferation of CD3/28-stimulated PBMCs.

FIGS. 4A to 4C show that MoT cell contact is required to functionally suppress proliferation of $CD4^+$ PBMC. In this assay, CFSE-labeled $CD4^+$ PBMC were stimulated with CD3 and CD28 antibodies for four days followed by flow cytometric analysis of proliferation (FIG. 4A). Four day spent supernatants from MoT cells were added to CD4+ PBMC that were stimulated with CD3/28 (FIG. 4B). MoT supernatant (FIG. 4B) stimulated 6 cell divisions while MoT cells (FIG. 4C) suppressed PBMC division compared to CD3/28 Stimulated controls (FIG. 4A). CFSE-labeled PBMC shift leftward in the flow cytometry diagram as they proliferate.

Immune checkpoint inhibitors do not attenuate MoT Treg suppressive activity. To determine if immune checkpoint inhibitors attenuate the MoT Treg suppressive activity, the inventors tested anti-PD-L1 (atezolizumab), anti-CCR4 (mogamulizumab), and anti-GITR blocking monoclonal antibodies (Mabs) for the ability to reverse MoT reg suppression (FIGS. 5A, 5B). Ipilimumab (anti-CTLA-4) and anti-PD-1 Mabs were not tested because they are not expressed on MoT cells (FIG. 1). CCR4 was previously reported to be present in Tregs[23]. Therefore, the inventors hypothesized that mogamulizumab might attenuate suppression of $CD4^+$ PBMC by MoT cells. None of the checkpoint inhibitor Mabs including anti-GITR reversed MoT cell-mediated suppression of $CD4^+$ PBMC (FIGS. 5D, 5F, and 5H). Incubation of each of the Mabs with $CD4^+$ PBMCs demonstrates that the Mabs do not suppress or inhibit $CD4^+$ PBMC proliferation (FIGS. 5C, 5E, and 5G). This result suggests that the mechanism of MoT cell suppression is not mediated via the PD-1/PD-L1 axis, CCR4, or GITR mechanisms.

FIGS. 5A to 5H show the results from CFSE assay demonstrates that anti-PD-1/PD-L1 axis, GITR and CCR4 are not involved in suppression of $CD4^+$ PBMC proliferation by MoT cells. (FIG. 5A) Unstimulated PBMC. (FIG. 5B) CD3/28-stimulated $CD4^+$ PBMC cell division without MoT cells. (FIG. 5C) Anti-GITR, (FIG. 5E) Anti-CCR4 mogamulizumab, and (FIG. 5G) anti-PDL-1 (atezolizumab) co-incubated with PBMCs. (FIG. 5D) Anti-GITR, (FIG. 5F) anti-CCR4 (mogamulizumab), and (FIG. 5H) anti-PDL-1 (atezolizumab) co-incubated with PBMCs and MoT cells (1:½ ratio).

Figures 6A, 6B, 6C, 6D:
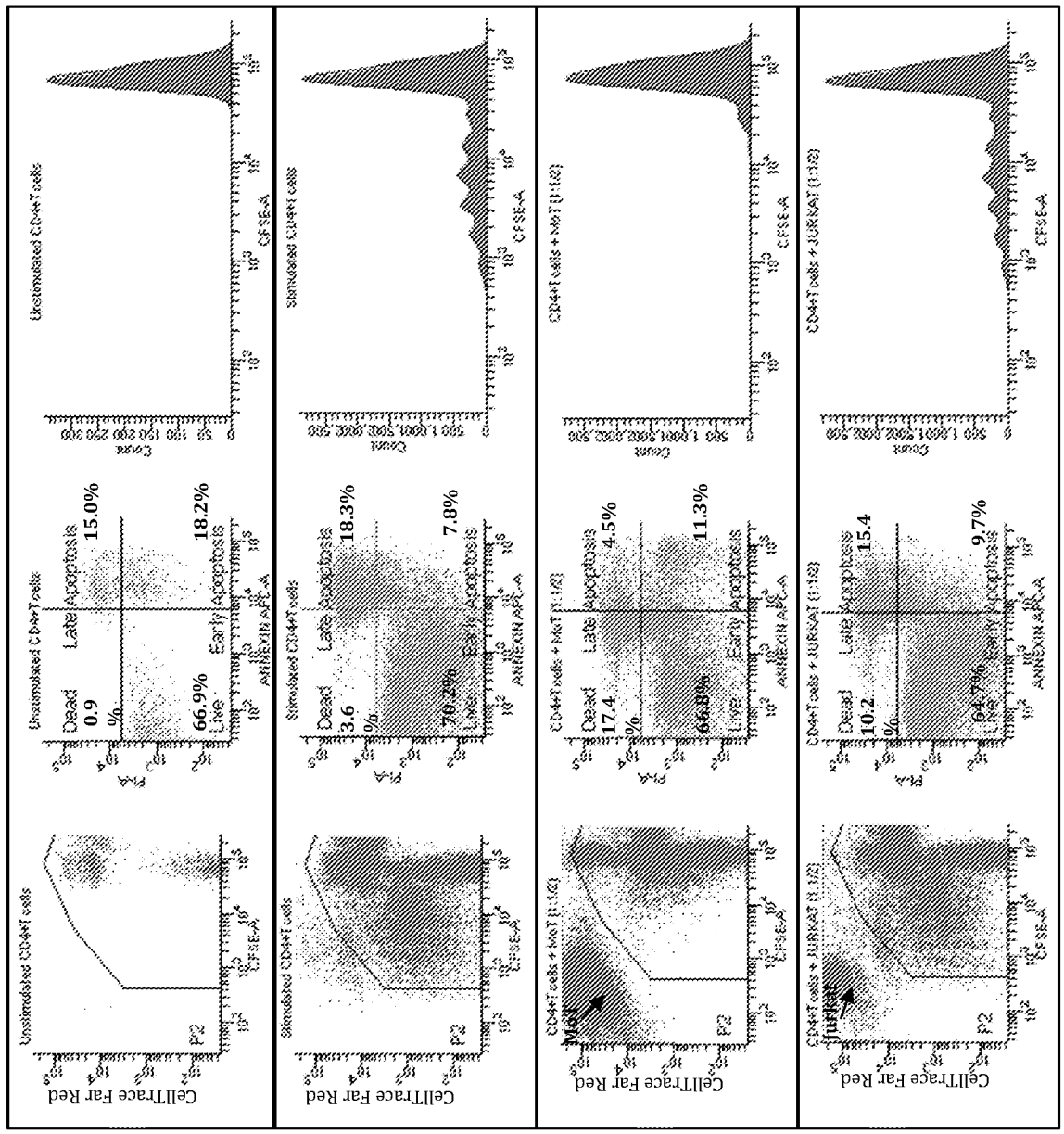
FIGS. 6A to 6D shows that MoT cells induce a distinct population of CD4+ PBMCs undergoing early apoptosis. MoT or Jurkat cells were labeled with CellTrace FarRed and CD4+ PBMC were labeled with CFSE prior to stimulation with anti-CD3 and anti-CD28.

MoT cells induce apoptosis of CD4+ PBMCs. To determine the mechanism of suppression of $CD4^+$ PBMC proliferation by MoT cells, the inventors performed an annexin V/propidium iodide (PI) experiment and evaluated the results by flow cytometry (FIGS. 6A to 6D). This study allows for visualization of early and late apoptosis, as well as, dead cells. FIGS. 6A to 6D demonstrate that MoT cells induce early apoptosis in a distinct population of $CD4^+$ PBMC (11.3%). MoT cells also induce cell death of 17.4% $CD4^+$ PBMC compared to 3.6% dead $CD4^+$ PBMC without MoT cells. The upper quadrants in the flow cytometry scatter plots in FIG. 6B (stimulated $CD4^+$ PBMC) and 6D (Jurkat co-incubation with $CD4^+$ PBMC) look remarkably similar to each other, and distinctly different than MoT co-incubation with $CD4^+$ PBMC (FIG. 6C). This result shows that MoT cells ultimately induce $CD4^+$ PBMC cell death, but clearly enter into an Annexin V-positive and PI-negative state (early apoptosis) prior to cell death.

FIGS. 6A to 6D shows that MoT cells induce a distinct population of $CD4^+$ PBMCs undergoing early apoptosis. MoT or Jurkat cells were labeled with CellTrace FarRed and $CD4^+$ PBMC were labeled with CFSE prior to stimulation with anti-CD3 and anti-CD28. (FIG. 6A) Unstimulated $CD4^+$ PBMCs; (FIG. 6B) anti-CD3/28-stimulated $CD4^+$ PBMC without MoT cells; (FIG. 6C) $CD4^+$ PBMC+MoT cells (ratio 1:½); (FIG. 6D) $CD4^+$ PBMC+Jurkat cells (ratio 1:½). Dot plots on the left side of each panel show CFSE-gated $CD4^+$ PBMC. Middle dot plot shows Annexin V/PI staining of gated $CD4^+$ PBMC. Right side of each panel shows histograms of $CD4^+$ PBMC proliferation.

Currently, the study of regulatory T cells is limited by the low prevalence of Tregs in peripheral blood and their heterogeneity upon isolation and stimulation. These challenges hinder development of therapies that specifically target Tregs. The inventors characterized $CD4^+$, $25^+$, $GITR^+$, $CTLA-4^-$, $PD-L1^+$, FoxP3 (weak) and CCR4 (weak) human MoT cells. As demonstrated in this report, MoT cells show weak expression of FoxP3 suggesting that they might be representative of peripheral Tregs.

Titrating MoT cell co-culture with $CD4^+$ PBMC shows MoT cell-dependent suppression. Although MoT is infected with HTLVII, and may even secrete HTLVII, supernatants from MoT do not suppress CD3/28-activated $CD4^+$ T cell proliferation; cell:cell contact is required and is directly dependent on the number of MoT cells in the culture. As MoT cells are titrated out of the culture, $CD4^+$ PBMC regain the ability to proliferate as shown in FIG. 2.

Prior studies demonstrated that HTLV infection is not sufficient to confer the Treg phenotype of MT2 cells[24]. Since MoT cells contain the HTLV-II genome it is possible that Tax from HTLV-II drives cell surface expression of CD25 (IL-2 receptor), but not IL-2 as reported previously[25] [26].

These data herein shows that the suppressive properties of MoT cells are not due to a soluble factor, and does not require the PD-1 or CTLA-4 axis since atezolizumab did not reverse suppression mediated by MoT cells on $CD4^+$ PBMC, and PD-1 and CTLA-4 are not expressed on the MoT cell surface. Prior proteomic analyses of cell surface proteins have identified >200 cell surface proteins on immortalized T cell lines and human T cells[27]. It could be possible that HTLVII Tax-mediated immortalization on MoT cells affects the activity. However, ectopic expression of Tax in Jurkat cells was not sufficient to induce expression of Treg cell surface markers[26]. Therefore, it is highly unlikely that HTLVII alone induces Treg phenotype or function.

Figures 7A, 7B:
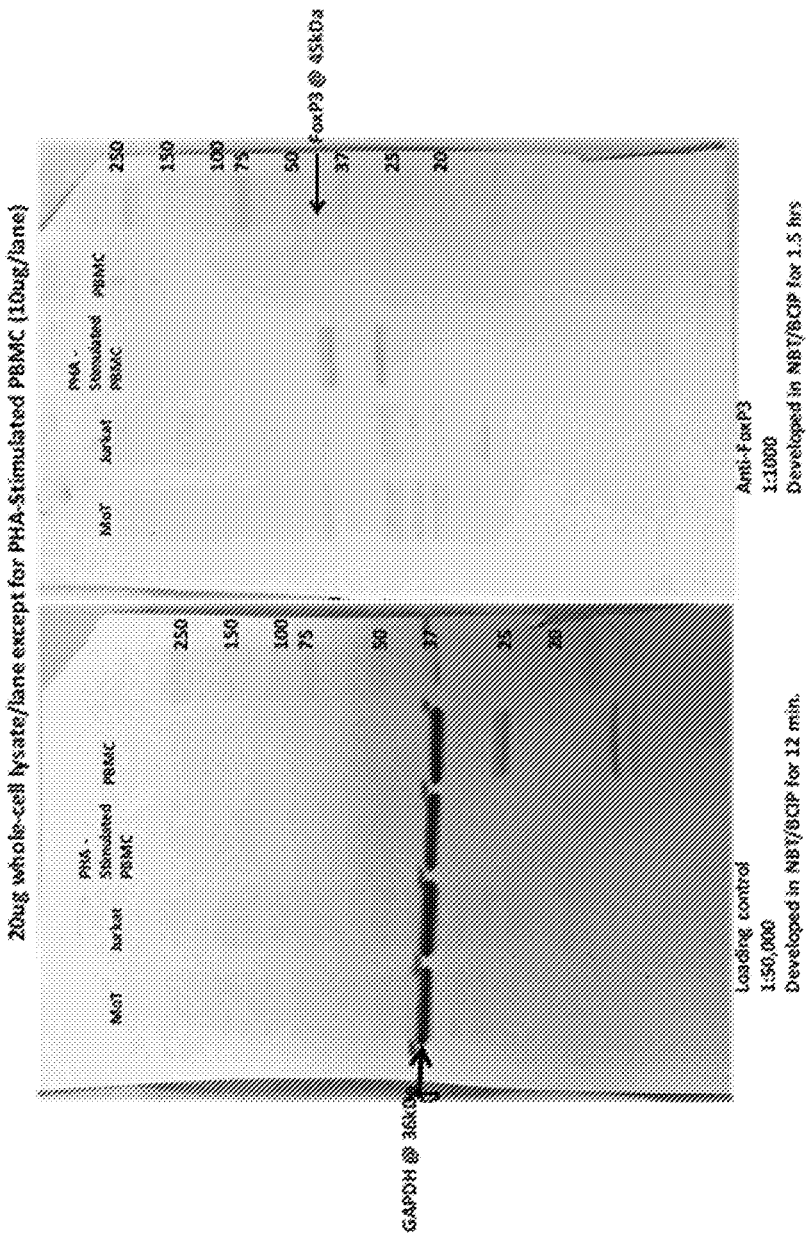
FIGS. 7A and 7B show that FoxP3 Immunoblot of MoT cells, Jurkat cells, PHA-stimulated PBMC and unstimulated PBMC. Bands observed on the immunoblot are representative of 20 ug/ml of lysate for each cell type. Immunoblot FIG. 7A was probed with anti-GAPDH Mab, showing the expected size of 36 kDa. Immunoblot FIG. 7B was probed with anti-FoxP3 Mab (eBioscience clone PCH101).

FIGS. 7A and 7B show that FoxP3 Immunoblot of MoT cells, Jurkat cells, PHA-stimulated PBMC and unstimulated PBMC. Bands observed on the immunoblot are representative of 20 ug/ml of lysate for each cell type. Immunoblot FIG. 7A was probed with anti-GAPDH Mab, showing the expected size of 36 kDa. Immunoblot FIG. 7B was probed with anti-FoxP3 Mab (eBioscience clone PCH101).

Tregs can limit antitumor responses and the presence of Tregs in solid tumors can impact clinical prognosis. Although current cancer therapies such as cyclophosphamide, sunitinib, and sorafenib can modulate Treg suppressive activity, these therapies are not Treg specific and likely impact anti-tumor T cells. Thus, there is a growing clinical need to selectively target Tregs in tumors while preserving the peripheral immune homeostasis. The inventors demonstrate herein, for the first time, the utility of MoT cells as a tool to identify drugs or cell surface proteins that functionally could overcome the immunosuppressive tumor microenvironment. Immune checkpoint inhibitor monotherapy such as anti-PD-L1, ant-CCR4, or ant-GITR did not attenuate MoT Treg suppressive activity. This shows that another cell surface molecule, different from PD-L1, CTLA-4, CCR4 and GITR, exists on MoT cells that mediates cell:cell contact-dependent suppression of $CD4^+$ PBMC proliferation.

To determine if MoT cells act as an IL-2 sink and absorb IL-2 produced by responding T cells, the inventors blocked the IL-2 receptor/CD25 with an IL-2R antibody. The CSFE proliferation assay was repeated using two independent donors (normal donor 82, PBMCs from an independent leukapheresis donor). Coincubation of an IL-2R antibody with MoT cells was not sufficient to interfere with or reverse the suppressive functions of MoT cells, indicating that the mechanism of suppression is not due to the MoT cells acting as an IL-2 sink. Similarly, antibodies that block LAG3/CD225 receptors did not attenuate the MoT suppressive activity.

Figure 8A:
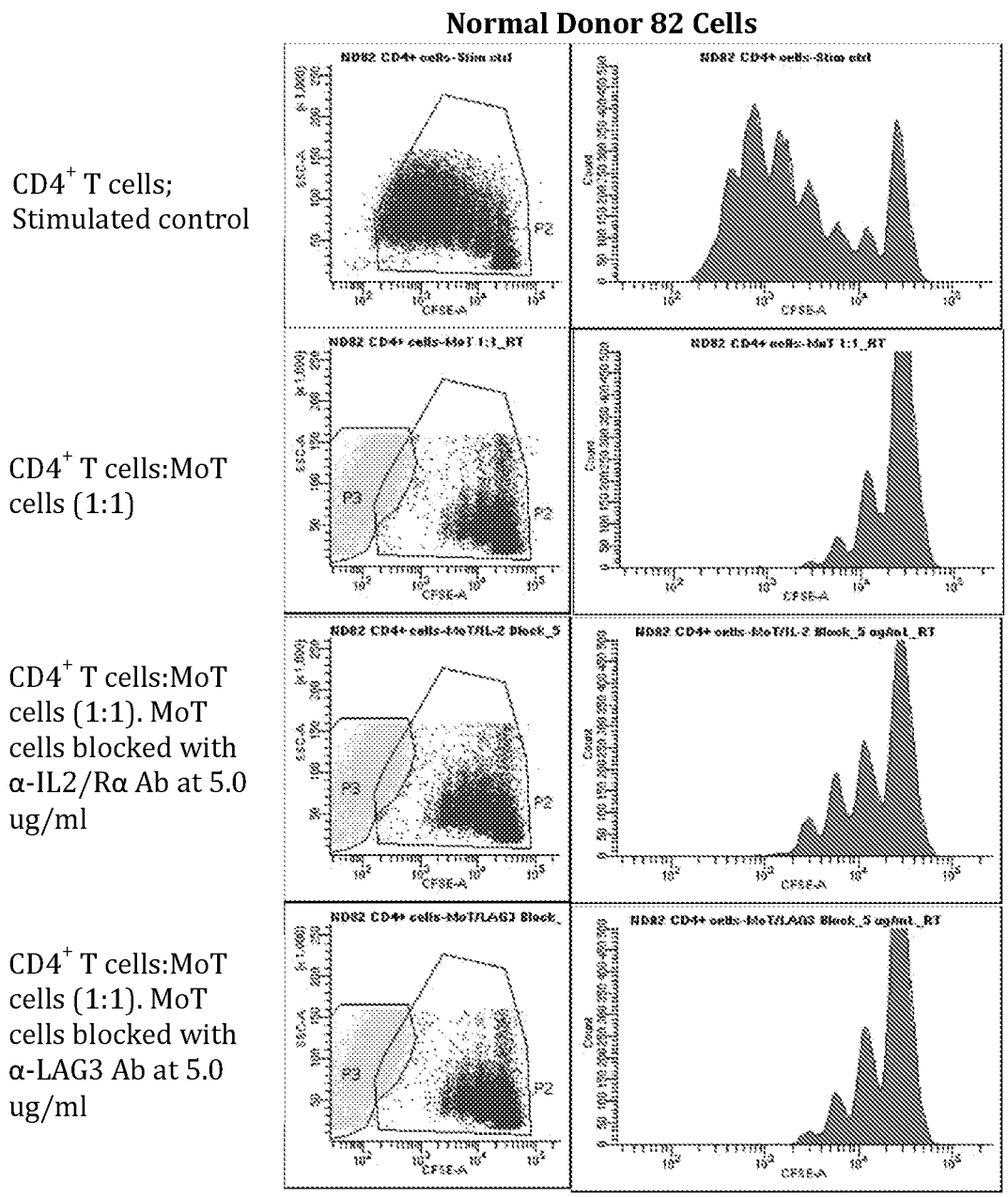
FIGS. 8A and 8B show that blockade of IL-2R or LAG3 is not sufficient to reverse the MoT cell suppression by flow cytometry in two independent donors.
Figure 8B:
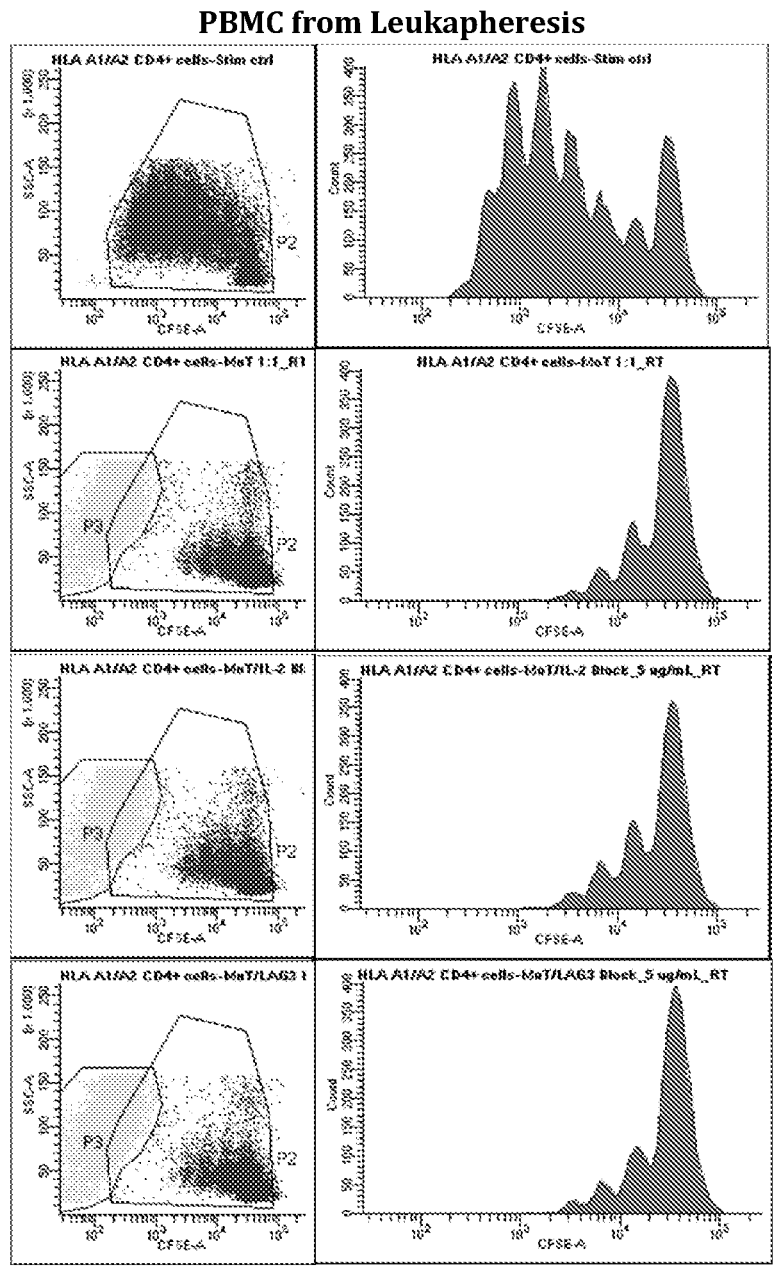

FIGS. 8A and 8B show that blockade of IL-2R or LAG3 is not sufficient to reverse the MoT cell suppression by flow cytometry in two independent donors. FIG. 8A represents cells from normal donor 28 and FIG. 8B represents PBMCs from an independent leukapheresis donor. This result suggests that the mechanism of MoT cell suppression is not mediated via IL-2R or LAG3 mechanisms. T cells stimulated with 5.0 ug/ml each of α-CD3 and CD28 antibody.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Belkaid Y, Blank R B, Suffia I. Natural regulatory T cells and parasites: a common quest for host homeostasis. Immunol Rev 2006; 212: 287-300.
2. Lanteri M C, O'Brien K M, Purtha W E, Cameron M J, Lund J M, Owen R E et al. Tregs control the development of symptomatic West Nile virus infection in humans and mice. J Clin Invest 2009; 119(11): 3266-77.
3. Roychoudhuri R, Eil R L, Restifo N P. The interplay of effector and regulatory T cells in cancer. Curr Opin Immunol 2015; 33: 101-11.
4. Nishikawa H, Sakaguchi S. Regulatory T cells in tumor immunity. Int J Cancer 2010; 127(4): 759-67.
5. Suri-Payer E, Amar A, Thorton A, Shevach E M. CD4+ CD25+ T cells inhibit both the induction and effector function of autoreactive T cells and represent a unique lineage of immunoregulatory cells. J Immunol 1998; 160(3): 1212-18.
6. Hill J A, Feuerer M, Tash K, Haxhinasto S, Perez J, Melamed R et al. Foxp3 transcription-factor-dependent and -independent regulation of the regulatory T cell transcriptional signature. Immunity 2007; 27(5): 786-800.
7. Shevach E M. From vanilla to 28 flavors: multiple varieties of T regulatory cells. Immunity 2006; 25(2): 195-201.
8. Asseman C, Mauze S, Leach M W, Coffman R L, Powrie F. An essential role for interleukin 10 in the function of regulatory T cells that inhibit intestinal inflammation. J Exp Med 1999; 190(7): 995-1004.
9. Collison L W, Workman C J, Kuo T T, Boyd K, Wang Y, Vignali K M et al. The inhibitory cytokine IL-35 contributes to regulatory T-cell function. Nature 2007; 450 (7169): 566-9.
10. Campbell D J, Koch M A. Phenotypical and functional specialization of FOXP3+ regulatory T cells. Nat Rev Immunol 2011; 11(2): 119-30.
11. Battaglia M, Stabilini A, Roncarolo M G. Rapamycin selectively expands CD4+CD25+FoxP3+ regulatory T cells. Blood 2005; 105(12): 4743-8.
12. Sauer S, Bruno L, Hertweck A, Finlay D, Leleu M, Spivakov M et al. T cell receptor signaling controls Foxp3 expression via PI3K, Akt, and mTOR. Proc Natl Acad Sci USA 2008; 105(22): 7797-802.
13. Strainic M G, Shevach E M, An F, Lin F, Medof M E. Absence of signaling into CD4(+) cells via C3aR and C5aR enables autoinductive TGF-beta1 signaling and induction of Foxp3(+) regulatory T cells. Nat Immunol 2013; 14(2): 162-71.
14. Wing K, Onishi Y, Prieto-Martin P, Yamaguchi T, Miyara M, Fehervari Z et al. CTLA-4 control over Foxp3+ regulatory T cell function. Science 2008; 322(5899): 271-5.
15. Fallarino F, Grohmann U, Hwang K W, Orabona C, Vacca C, Bianchi R et al. Modulation of tryptophan catabolism by regulatory T cells. Nat Immunol 2003; 4(12): 1206-12.
16. Zeng H, Zhang R, Jin B, Chen L. Type 1 regulatory T cells: a new mechanism of peripheral immune tolerance. Cell Mol Immunol 2015; 12(5): 566-71.
17. Bluestone J A, Buckner J H, Fitch M, Gitelman S E, Gupta S, Hellerstein M K et al. Type 1 diabetes immunotherapy using polyclonal regulatory T cells. Sci Transl Med 2015; 7(315): 315ra189.
18. Ezzelarab M B, Thomson A W. Adoptive Cell Therapy with Tregs to Improve Transplant Outcomes: The Promise and the Stumbling Blocks. Curr Transplant Rep 2016; 3(4): 265-274.
19. Fisher S A, Lamikanra A, Doree C, Gration B, Tsang P, Danby R D et al. Increased regulatory T cell graft content is associated with improved outcome in haematopoietic stem cell transplantation: a systematic review. Br J Haematol 2017; 176(3): 448-463.
20. Wang W, Lau R, Yu D, Zhu W, Korman A, Weber J. PD1 blockade reverses the suppression of melanoma antigen-specific CTL by CD4+CD25(Hi) regulatory T cells. Int Immunol 2009; 21(9): 1065-77.
21. ClincalTrials.gov. Safety and Efficacy of CLBS03 in Adolescents With Recent Onset Type 1 Diabetes (The Sanford Project T-Rex Study). In, 2017.
22. Schneider U, Schwenk H U, Bornkamm G. Characterization of EBV-genome negative "null" and "T" cell lines derived from children with acute lymphoblastic leukemia and leukemic transformed non-Hodgkin lymphoma. Int J Cancer 1977; 19(5): 621-6.
23. Plitas G, W. K, Carlson J, Cimaglia N, Morrow M, Rudensky A Y. Phase I/II study of mogamulizumab, an anti-CCR4 antibody targeting regulatory T cells in advanced cancer patients. J Clin Oncology 2016; 34: 15-Supplemental.
24. Hamano R, Wu X, Wang Y, Oppenheim J J, Chen X. Characterization of MT-2 cells as a human regulatory T cell-like cell line. Cell Mol Immunol 2015; 12(6): 780-2.
25. Ballard D W, Bohnlein E, Lowenthal J W, Wano Y, Franza B R, Greene W C. HTLV-I tax induces cellular proteins that activate the kappa B element in the IL-2 receptor alpha gene. Science 1988; 241(4873): 1652-5.
26. Tarasevich A, Filatov A, Pichugin A, Mazurov D. Monoclonal antibody profiling of cell surface proteins associated with the viral biofilms on HTLV-1 transformed cells. Acta Virol 2015; 59(3): 247-56.
27. Bausch-Fluck D, Hofmann A, Bock T, Frei A P, Cerciello F, Jacobs A et al. A mass spectrometric-derived cell surface protein atlas. PLoS One 2015; 10(3): e0121314.

What is claimed is:

1. A method for screening one or more agents that modulate Regulatory T cell (Treg) activity, the method comprising the steps of:
   incubating a population CD4+ cells isolated from human blood peripheral mononuclear cells with American Type Culture Collection deposit number CRL-8066 MoT cells in the presence and absence of one or more agents suspected of modulating Treg activity;
   detecting activation of the CD4+ cells in the presence and absence of the one or more agents; and
   comparing the activation of the CD4+ cells in the presence and absence of the one or more agents, wherein a change in activation in the presence of the one or more agents relative to the activation of the CD4+ cells following incubation in the absence of the one or more agents indicates that the one or more agents are modulators of Treg activity.

2. The method of claim 1, wherein the one or more agents inhibit at least one of: autoimmune disease, or graft-versus-host disease.

3. The method of claim 1, wherein the one or more agents increase an anti-tumor immune response in patients treated with immune checkpoint therapy.

4. The method of claim 1, wherein the activation of CD4+ cells is measured by cell proliferation.

5. The method of claim 1, wherein the activation of CD4+ cells is measured by expression of at least one of CD25, CD69, HLA-DR, CD26, or CD40L.

6. The method of claim 1, wherein the one or more agents prevent CD4+ cell apoptosis.

7. The method of claim 1, wherein the one or more agents prevent CD4+ cells from entering into Annexin V-positive and PI-negative state or early apoptosis phase.

8. The method of claim 1, wherein the one or more agents prevents CD4+ cell proliferation.

9. The method of claim 1, wherein a decrease in the expression of at least one of IL17, IL17F, IL23R, RORC or IL26 after incubation in the presence of the one or more agents is indicative of the agent being an inhibitor of Treg in vitro, or wherein an increase in the expression of at least one of TGFbeta, IL-1, IL-2, IL-6 or TNF after incubation in the presence of the one or more agents is indicative of the agent being an activator of Treg in vitro.

10. The method of claim 1, wherein the one or more agents is selected from a small molecule; polypeptide; antibody; antibody fragment; azole-containing compounds; cholesterol derivative compounds; retinoid derivative compounds; shRNA/siRNA; neutralizing/blocking antibodies; tryptophan derivative compounds; Vitamin D derivatives; or molecules known to inhibit fever, inflammation, allergy, or regulatory T (Treg) cell differentiation factor.

11. The method of claim 1, further comprising testing a combination of two or more agents to increase Treg activity, or decrease Treg activity.

12. A method for screening one or more agents that modulate Regulatory T cell (Treg) activity, the method comprising the steps of:
(a) providing a population CD4+ cells isolated from human blood peripheral mononuclear cells;
(b) contacting the CD4+ cells with American Type Culture Collection deposit number CRL-8066 MoT cells;
(c) incubating the CD4+ cells and the MoT cells in the presence and absence of an agent suspected of modulating Treg activity;
(d) detecting activation of the CD4+ cells in the presence and absence of the agent; and
(e) comparing the activation of the CD4+ cells in the presence and absence of the agent, wherein a change in activation following incubation in the presence of the agent relative to the activation of the CD4+ cells following incubation in the absence of the agent indicates that the agent is a modulator of Treg activity.

13. The method of claim 12, wherein the one or more agents inhibit at least one of:
autoimmune disease, or graft-versus-host disease.

14. The method of claim 12, wherein the one or more agents increase an anti-tumor immune response in patients treated with an immune checkpoint inhibitor therapy.

15. The method of claim 12, wherein the activation of CD4+ cells is measured by cell proliferation.

16. The method of claim 12, wherein the one or more agents prevents CD4+ cell proliferation.

17. The method of claim 12, wherein the activation of CD4+ cells is measured by expression of at least one of CD25, CD69, HLA-DR, CD26, CD40L.

18. The method of claim 12, wherein the one or more agents prevent CD4+ cell apoptosis.

19. The method of claim 12, wherein the one or more agents prevent CD4+ cells from entering into Annexin V-positive and PI-negative state or early apoptosis phase.

20. The method of claim 12, wherein a decrease in the expression of at least one of IL17, IL17F, IL23R, RORC or IL26 after incubation in the presence of the one or more agents is indicative of the agent being an inhibitor of Treg in vitro, or wherein an increase in the expression of at least one of TGFbeta, IL-1, IL-2, IL-6 or TNF after incubation in the presence of the one or more agents is indicative of the agent being an activator of Treg in vitro.

21. The method of claim 12, wherein the one or more agents is selected from a small molecule; polypeptide; antibody; antibody fragment; azole-containing compounds; cholesterol derivative compounds; retinoid derivative compounds; shRNA/siRNA; neutralizing/blocking antibodies; tryptophan derivative compounds; Vitamin D derivatives; or molecules known to inhibit fever, inflammation, allergy, or regulatory T (Treg) cell differentiation factor.

22. The method of claim 12, further comprising testing a combination of two or more agents to increase Treg activity, or decrease Treg activity.

23. A method of evaluating a candidate drug believed to be useful in modulating Regulatory T cell (Treg) activity, the method comprising:
(a) obtaining a first population of CD4+ cells isolated from human blood peripheral mononuclear cells from a patient;
(b) administering a candidate drug to the patient;
(c) obtaining a second population of CD4+ cells isolated from human blood peripheral mononuclear cells from the patient after the administration of the candidate drug;
(d) contacting the first and second population of CD4+ cells isolated from human blood peripheral mononuclear cells from the patient with American Type Culture Collection deposit number CRL-8066 MoT cells to activate the CD4+ cells;
(e) determining if the candidate drug modulates the CD4+ cells activation, wherein a change in activation between the first population of CD4+ cells and the second population of CD4+ cells indicates that the agent is a modulator of Treg activity.

* * * * *